United States Patent [19]

Schiffman et al.

[11] 4,427,660

[45] Jan. 24, 1984

[54] FORMYL-METHIONYL CHEMOTATIC PEPTIDE ANTIBIOTIC CONJUGATES USEFUL IN TREATING INFECTIONS

[75] Inventors: Elliott Schiffman, Chevy Chase, Md.; Leonard C. Altman, Seattle, Wash.

[73] Assignee: Research Corporation, New York, N.Y.

[21] Appl. No.: 354,357

[22] Filed: Mar. 3, 1982

[51] Int. Cl.$^3$ .................... A61K 37/00; C07C 103/52
[52] U.S. Cl. .............................. 424/177; 260/112.5 R
[58] Field of Search ................... 424/177; 260/112.5 R

[56] References Cited

PUBLICATIONS

Chem. Abst. vol. 74, (1971) 30702A.
Chem. Abstr. vol. 88, (1978) 35718j.
Biochem. & Biophys. Res. Commun. 74, 1977, 810–817.
Biochem. & Biophys. Res. Commun. 80, 1928, 464–471.

Primary Examiner—Delbert R. Phillips
Attorney, Agent, or Firm—Scully, Scott, Murphy and Presser

[57] ABSTRACT

A group of synthetic N-formyl methionine tri and tetra peptides in covalent combination with antibiotics are useful in treating infections. These peptideantibiotic conjugates exhibit a high degree of chemotactic activity for polymorphonuclear leukocytes and monocytes while simultaneously inhibiting the growth of microorganisms. The use of chemotactic peptide-silver sulfadiazine conjugates is particularly effective for treating burns.

15 Claims, 4 Drawing Figures

THE NMR SPECTRUM REVEALS ONLY THE EXPECTED PROTON INTERACTIONS FOR THE SINGLE COMPOUND FMLP-SDZ

FORMYL-METHIONYL CHEMOTATIC PEPTIDE ANTIBIOTIC CONJUGATES USEFUL IN TREATING INFECTIONS

BACKGROUND OF THE INVENTION

1. Field of the Invention

This invention relates to novel synthetic N-formyl peptides in combination with antibiotics. More particularly, to certain N-formyl tri- and tetra-peptides useful as chemoattractants in combination with antibiotics such as silver sulfadiazine useful in inhibiting microorganisms.

2. Description of the Prior Art

Chemotaxis is the directed movement of cells along an increasing chemical gradient. Certain naturally occurring substances, such as C5a (a serum factor derived from complement) and compounds elaborated by bacteria, have been reported as being leukoattractants, i.e., having chemotactic activity for leukocytes. In addition to their chemotatic activity, such substances have been found to induce lysosomal enzyme secretion from the leukocytes, particularly in the presence of cytochalasin B. The size, complexity, and unknown structure of most of these leukoattractant substances, have precluded any definitive analysis of the structural of molecular basis of their chemotactic activity. It has been established that leukoattractants produced by *E. coli, which are extremely potent and present in low concentrations in the cell culture medium, have as their active components small, heterogeneous peptides with blocked amino groups, but their low concentration levels have hampered further characterization.*

Recent studies have produced substantial evidence to the effect that the naturally occurring leukoattractants elaborated by bacteria, together with the phenomenon of chemotaxis, play a major role in the first line of defense of the human body to bacterial infection. Thus, it is believed that the phagocytic or defense leukocytes, i.e., neutrophils, macrophages, basophils, and eosinophils, accumulate at sites of infection, in part, as a response to the leukoattractants secreted by the invading organisms. The leukoattractants then induce secretion from the phagocytes of the lysosomal enzymes which, in turn, attack and destroy the invading organisms. In addition, some of the phagocytes participate in the laying down of new connective tissue after the infection has been cured. Therefore, their appearance at the site of pathology is important in two respects, i.e., destroying the invading organisms and restoring the damaged tissue.

Silver sulfadiazine is the antibiotic commonly used to treat burns. However, silver sulfadiazine inhibits the migration of polymorphonuclear leukocytes and monocytes into the area of infection treated with the antibiotic. Therefore, a need exists for a method of stimulating the migration of polymorphonuclear leukocytes and monocytes into the area containing the antibiotic. Based upon the theory that leukoattractants in combination with antibiotics will promote migration of polymorphonuclear leukocytes and monocytes into an area otherwise inhibited by the antibiotic, experimental procedures were disclosed to produce a synthetic leukoattractant-antibiotic complex suitable for the purpose.

The following publications are herein incorporated by reference.

(1) Aswanikumar et al, Biochemical and Biophysical Research Communications 74:810, 1977;

(2) Altman et al, Journal of Immunology, 119:199, 1977;

(3) Warden et al, Annals Surgery, 181:363, 1975;

(4) Schiffmann et al, Proc. Nat. Sci. USA, 72:1059, 1975

(5) Altman et al, Journal of Surgical Research, 22:616, 1975;

(6) Fikrig et al, Ann. Surg. 186:746, 1977. Altman et al, Fed. Procedings 40:1103, 1981.

SUMMARY OF THE INVENTION

It is, accordingly, a primary object of the present invention to provide novel synthetic leukoattractant antibiotic conjugates of relatively high potency.

Another object of the invention is to provide improved synthetic leukoattractant antibiotic complexes in accordance with the preceding object, which exhibit a high degree of chemotactic activity for phagocytic leukocytes while not inhibiting the action of the antibiotic.

A further object of the invention is to provide improved synthetic leukoattractants in accordance with the preceding objects, which exhibit a high degree of lysosomal enzyme secretion-inducing activity while not inhibiting the action of the antibiotic.

Still another object of the invention is to provide improved synthetic leukoattractant-antibiotic conjugates in accordance with the preceding objects, which, when administered to a localized area of an animal body, are capable of chemotactically attracting phagocytic leukocytes to such localized area even in the presence of active antibiotic.

An additional object of the invention is the covalent coupling of the leukoattractant peptide to the antibiotic to form a leukoattractant-antibiotic conjugate.

Still another object of the invention is to covalently bind the antibiotic silver sulfadiazine to the leukoattractant.

Another object of the invention is to treat septic trama, such as burns, with the application of a pharmacologically effective compound containing the leukoattractant-antibiotic complex.

Another object of the invention is to produce anti-tumor conjugates of f-met peptides in combination with anti-tumor agents.

The above and other objects are achieved in accordance with the present invention by providing novel synthetic N-formyl peptides selected from the group consisting of f-Met-Leu-Phe-R, f-Met-Met-Phe-R, f-Met-Met-Met-R, f-Nle-Leu-Phe-R, f-Met-Leu-Phe-Lys-R, wherein R is an antibiotic, such as silver sulfadiazine or other bactercidal or fungacidal agent.

BRIEF DESCRIPTION OF THE DRAWINGS

Various other objects, features and attendant advantages of the present invention will be more fully appreciated as the same becomes better understood from the following detailed description when considered in connection with the accompanying drawings.

DETAILED DESCRIPTION OF THE PREFERRED EMBODIMENTS

Figure 1:
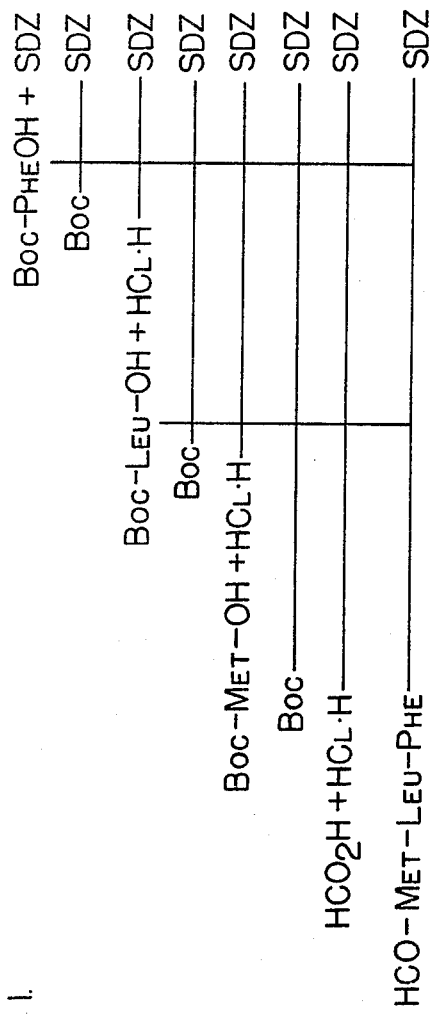
FIG. 1-Synthetic steps in synthesis of the chemotactic peptide-antibiotic conjugate formyl-Met-Leu-phe-silver sulfadiazine.

It will be understood that in the above definitions of the N-formyl peptides of the present invention and in the following discussion, all abbreviations are the standard abbreviations employed in peptide chemistry, and all amino acid residues referred to are L-amino acid residues. For improved clarity, these abbreviations are listed below.

Met=methionyl
Leu=leucyl
Phe=phenylalamine
Nle=norleucyl
Lys=lysyl
f=N—formyl
t-Boc=tert-butyloxycarbonyl The N-formyl peptides of the present invention may be readily prepared by the Merrifield solid-phase peptide synthesis technique well known in the art and described, for example, by Steward and Young, "Solid Phase Peptide Synthesis" (W. H. Freeman & Co., San Francisco, 1969). Formylation of the synthesized peptide may be carried out by the method of Sheehan and Yang (J. Am. Chem. Soc., Volume 80, Page 1154, 1958). The peptide synthesis is commenced from the carboxyl terminal end of the peptide by coupling the appropriate amino acid, i.e., either L-phenylalanine, L-methionine or L-lysine, to a suitable resin support, such as chloromethylated resin, a hydroxymethyl resin or a benzhydrylamine resin. The coupling reaction is carried out with the α-amino group of the amino acid protected with a protecting group, such as t-Boc. Following this coupling reaction, the α-amino protecting group is removed, such as by using trifluoroacetic acid in methylene chloride, trifluoroacetic acid alone or HCl in dioxane, with the deprotection being carried out at a temperature between about 0° C. and room temperature. Thereafter, each succeeding amino acid in the sequence is coupled in the same manner step-wise in the desired order, with the aid of a carboxyl group-activating compound such as dicyclohexylcarbodiimide, to thereby obtain the proper peptide sequence.

After the final α-amino protected amino acid in the sequence, i.e., either L-methionine or L-norleucine, has been coupled, the deprotection step is carried out by treatment with a reagent such as hydrogen chloride which not only cleaves the α-amino protecting group from the final amino acid, but also cleaves the peptide from the resin support. When a benzhydrylamine resin has been used as the resin support, the peptide thereby cleaved from the resin will be in the carboxyl terminal amide from (wherein R is $NH_2$). When a chloromethylated resin or a hydroxy methyl resin has been used as the resin support, the peptide cleaved from the resin support will be in the form of the carboxyl terminal benzyl ester, which may then be readily converted by methods well known in the art to the free acid from (wherein R is OH) or the carboxyl terminal amide form of the peptide.

Formylation of the peptide is then carried out with formic acid and acetic anhydride, in accordance with the method of Sheehan and Yang, supra. Unformylated peptide may be removed from the reaction mixture by passage of the peptide through Dowex 50 ion exchange resin in acid form (Dow Chemical Co., Midland, Mich.).

The N-formyl tri- and tetra-peptides in accordance with the present invention have been found to exhibit an exceptionally high degree of chemotactic activity for phagocytic leukocytes, as well as a correspondingly high degree of lysosomal enzyme secretion-inducing activity. For example, with respect to each of these properties, the N-formyl peptides of the present invention range from 500 (f-Met-Leu-Phe-Lys-OH) to 5,000 (f-Met-Leu-Phe-OH) times more active than f-Met-Phe-OH, the most active of the N-formyl peptides reported in the Schiffmann et al publication referred to above. Such high activity renders the N-formyl peptides of the present invention highly potent leukoattractants suitable for clinical use in various biomedical applications. For example, in combination with antibiotics, such as silver sulfadiazine, that inhibit both the infecting microorganism and the migration of polymorphonuclear leukocytes and monocytes into the area. The presence of the leukoattractant promotes the migration of polymorphonuclear leukocytes and monocytes even in the presence of antibiotics, such as silver sulfadiazine. Moreover, the action of the antibiotic remain active allowing the treatment of the infection by both active antibiotic and the defenses carried by polymorphonuclear leukocytes and monocytes.

Infection is the leading cause of morbidity and mortality in burn patients, with many of the infections originating in the burned tissues, therefore it is critical that the burned tissue be treated with antibiotics such as silver sulfadiazine. A complication is created by the fact that silver sulfadiazine further depresses the already depressed chemotaxis of circulating leukocytes in burn patients. Polymorphonuclear Leukocytes and monocytes are highly important in promoting healing in burns and other tissue trama. Therefore, a topical agent which provides antimicrobial activity and chemotactic activity to attract polymorphonuclear leukocytes and monocytes to the burn site, is far superior to presently available agents for the treatment of burns and the prevention of burn wound infection.

One of the leukoattractants, f-Met-Leu-Phe in addition to attracting polymorphonuclear leukocytes and monocytes, also promotes histamine release from basophil leukocytes. It also promotes lysosomal enzyme release and both hydrogen peroxide and superoxide anion production by polymorphonuclear leukocytes. Therefore, the f-Met-Leu-Phe-Ag-Sulfadiazine complex has the ability to hasten the healing of burn wounds by producing chemical escar debridement and inhibiting microbial infection. The application of the chemotactic-antibiotic conjugate can be applied to create a concentration gradient wherein the concentration is high at the infection site and progressively lower in the surrounding tissue, thereby creating a chemoattractant gradient to atrract polymorphonuclear leukocytes and monocytes.

Antifungal drugs can also be conjugated to the N-formyl chemoattractants. Cutaneous fungal infections can be treated with compounds such as f-met-leu-phe-fungacide, wherein the antifungal agent is miconazole, clotrimazole, nystatin or amphotericine B. Additional information on these and other anti-fungal agents for use with the N-formyl chemoattractants can be found in the following publications incorporated by reference:

1. Havey S. C.: Antiseptics and disinfectants: fungicides; ectoparasiticides in The Pharmacological Basis of Therapeutics. Sixth Edition, Macmillan Publishing Co., Inc., 1980, p. 964–987;

2. Sande M. A., Mandell G. L.: Antimicrobial Agents (continued). Miscellaneous antibacterial agents; antifungal and antiviral agents in The Pharmacological Basis of Therapeutics. Sixth Edition, Macmillan Publishing Co., Inc., 1980, p. 1222-1248.

The above results indicate that the N-formyl peptide leukoattractant-antibiotic conjugates of the present invention may be highly useful in the treatment of various localized infections. Thus, by administering a chemotactically effective amount of the N-formyl peptide-antibiotic complex to the effected area of the body, a greater influx of phagocytic leukocytes into the affected area would be produced, resulting in enhanced destruction of the invading organisms, as well as enhanced restoration of the damaged tissue, while allowing the antibiotic action on infecting microorganisms.

The topical cream vehicle for silver sulfadiazine as it is presently marketed is a soft, white cream. The vehicle consists of white petrolatum USP, stearyl alcohol USP, isopropyl myristate, sorbitan monooleate, polyoxyl 40 stearate USP, propylene glycol USP and water with methylparaben USP 0.3% as preservative. In order to reduce the frequency of application and increase the clinical usefulness of f-met-peptide-antimicrobial/antifungal conjugates, they can be delivered in slow release vehicles. Examples of such vehicles are polymers of 2 hydroxyethyl methacrylate and methyl methacrylate. These polymers can be prepared as small spheres or as sheets of polymer impregnated with the conjugate for placement over the local wound or infection.

It should be noted that the high chemotactic and lysosomal enzyme secretion-inducing activities of the N-formyl peptides of the present invention, are not exhibited by the corresponding unformylated peptides. Moreover, such high activities are exceedingly specific to the particular peptide structures of these leukoattractants since very small changes in structure, either in regard to the constituent amino acid residues or in regard to their positions in the peptide chain, result in substantial decreases in activity. For example, f-Met-Phe-Leu-OH, which differs from the f-Met-Leu-Phe-OH of the present invention only in the inversion of the terminal two amino acid residues, is 500 times less active than f-Met-Leu-Phe-OH.

Chemoattractants which interact with leukocytes at the same binding site for formylated peptides and which also possess antimicrobial activity have been described (Aswanikumar et al. 1978. Biochem. Biophys. Res. Commun. 80, 464-471). These studies, document the dual activities of the antimicrobial compounds gramicidin, bacitracin, and tyrocidin. These substances are relatively weak chemoattractants ($10^{-5}$ to $10^{-6}$ M) and possess ionophoric properties, the latter of which would make them unsuitable for the purposes of promoting wound healing in burns. The conjugate F Met-Leu-Phe-SDZAg does not have the deleterious effect of an ionophore, but retains the desired chemotactic and antimicrobial activities. In addition, the chemotactic portion of the conjugate can be modified to produce compounds with a variety of potencies without affecting the antimicrobial properties.

It has been shown that a melanotropin-daunomycin conjugate can bind to and lyse cultured murine melanoma cells (Varga et al 1977. Nature 267, 56-58). Daunomycin, an antitumor agent, can be coupled to F Met peptides for localized treatment of malignant lesions. Alternatively, the chemotactic peptide can be conjugated to melanotropin to produce a compound that should show specificity of binding to melanoma cells. In both cases, the attractant portion of the conjugate enhances phagocytic accumulation at the site of the tumor with subsequent attack on the malignant cells. It is readily seen that possibilities exist for a great variety of compounds in which the peptide attractants are conjugated to specific hormones, mediators, and growth factors which would bind to their target tissue. Thus, thyroxine, ACTH, substance P, and insulin can, in their appropriate conjugates, be used to direct a phagocytic attack upon tumors in specific organs. Advantage might be taken of the high affinity for bone characteristic of tetracycline to treat osteoid malignancies with a conjugate of this antibiotic and an attractant.

In the design of bifunctional pharmaceuticals, it is prudent to take into account the capacities of the host's tissues to inactivate these compounds. Oxidation and hydrolysis are two mechanisms by which inactivation may be accomplished at the relatively external sites of pathological events with which we are concerned. With respect to the formylated peptide protion of a conjugate, this may be rendered more resistant to biological oxidation by substituting norleucine for methionine (Clark et al 1980. J. Immunol. 124, 2020-2026). Such a modification producing a longer-lived drug may well amplify the beneficial effects to the conjugate.

With respect to designing compounds that are resistant to hydrolysis, it is possible to substitute methylene bridge for peptide bonds between amino acid residues.

The invention is further illustrated by way of the following examples.

EXAMPLE 1

Synthesis of f-Met-Leu-Phe-Oh

Chloromethylated resin is first reacted with the triethylammonium salt of t-Boc-L-phenylalanine in ethanol at 85° C. for a period of 48 hours. The attached amino acid residue is then deprotected by treating the peptide-resin with a 1:1 solution of trifluoroacetic acid-methylene chloride (3 times for 15 minutes each). The peptide-resin is then subjected to successive repetitions of the above-described coupling procedure, but carried out in the presence of dicyclohexylcarbodiimide, and substituting for the t-Boc-L-phenylalanine the following α-amino protected amino acids in the following order: t-Boc-L-leucine and t-Boc-L-methionine. Removal of the α-amino protecting group following the coupling step with the t-Boc-L-leucine is performed as described for the deprotection of the t-Boc-L-Phe-resin. After coupling of the t-Boc-L-methionine, removal of the protecting group and cleavage of the peptide from the resin is then accomplished by reaction with liquid hydrogen fluoride for 30 miinutes at 0° C., anisole being added to the hydrogen fluoride to provide a free radical scavenger. The HF-treated resin is then washed with ethyl ether to remove anisole and its reaction products. The peptide is then extracted with glacial acetic acid and lyophilized. The peptide is purified by countercurrent distribution (100 transfers in n-butanol acid:water, 4:1:5). The peptide is considered pure if it shows only one spot on high voltage electrophoresis at pH 5.0, and in at least two thin-layer chromatography systems (usually n-butanol:acetic acid:water, 4:1:5 or cellulose and chloroform:methanol:acetic acid:water, 65:30:4:1 on silica gel). Both ninhydrin and nonspecific $I_2$ stains are used to visualize the peptide.

The peptide is then formylated in the following manner. The peptide is dissolved in 97 percent formic acid, and the mixture is kept in an ice bath. Acetic anhydride is then slowly added to one third the volume of the initially added formic acid, keeping the mixture cold. The mixture is then taken out of the ice bath and allowed to come to room temperature. After 4 hours at room temperature, the whole solution is diluted with 20-fold excess of water, the solution is lyophilized, and volatile matter removed, leaving the formylated peptide. The formylated peptide is purified by dissolving it in water, bringing the pH to 5, and then passing the mixture over Dowex 50 ion exchange resin in acid form. The effluent of the column is then lyophilized, resulting in pure formulated peptide free of any unformylated peptide.

In like manner, the other N-formyl peptides in accordance with the present invention may be readily synthesized by employing the appropriate $\alpha$-amino protected amino acids. The carboxyl terminal amide form of the peptide may be readily obtained, for example, by using a benzhydrylamine resin as the resin support in place of the chloromethylate resin.

EXAMPLE 2

Assay of Chemotactic Activity

Rabbit polymorphononuclear leukocytes (neutrophils) were obtained 12 to 14 hours after the intraperitoneal injection of 0.1 percent glycogen, as described in Becker et al (Z. Immunitaetsforsch Exp. Klin. Immunol., Volume 143, Page 466 1972). They were washed in Hanks' balanched salt solution containing 0.01 M tris (hydroxymethyl) aminomethane, pH 7.2, 1 mg/ml of glucose, and 1 mg/ml of crystalline bovine serum albumin. The Hanks' balanced salt solution was the buffer used throughout the work.

The assay employed a modified Boyden chamber as described by Becker et al, supra. Briefly, 1 ml of washed peritoneal netrophils containing $2.5 \times 10^6$ cells was added to the upper compartment of the modified Boyden chamber separated from 1 ml of peptide solution by a 25 mm diameter filter of 0.6 $\mu$m average pore size. The loaded chambers were incubated for 30 minutes at 37° C. This time interval was chosen as giving, for the particular batch of filters used, the greatest difference between the number of cells moving into the filter with no peptide in the lower compartment (background) and the maximum number of cells moving into the filter when stimulated by peptide. At the end of the incubation the filters were removed and stained and the number of cells in five high-power (400 magnification) fields (5 HPF) were counted and averaged. The results reported are the means of duplicate chambers.

The migration enhancing activities of different peptides were compared essentially as described by Schiffmann et al (J. Immunol., Volume 144, Page 1830, 1975) and Showell et al (J. Immunol., Volume 116, Page 99, 1976). In measuring the relative activity of the peptides, a peptide was diluted so that each concentration was one quarter that of the next higher concentration. The concentrations of peptides were chosen on the basis of preliminary experiments to cover the range giving minimum to maximal activity. The chemotactic activity plotted against the logarithm of the molar concentration of peptide yielded a sigmoidal-shaped dose-response curve. Different peptides tested at the same time with the same cells gave curves which were parallel to each other in their linear portions and had the same maximum. The activities of the different peptides are reported as the $ED_{50}$, i.e., the concentration of chemotactic factor giving 50 percent of the maximum activity.

The results of the assay of chemotactic activity are reported in Table 1 below, for each of the N-formyl peptides of the present invention, and for purposes of comparison, for the two most active prior art N-formyl peptides previously described in the Schiffmann et al publication referred to above. The results are reported as the means $ED_{50} \pm SE$ (standard error) as determined by at least three separate experiments. In this assay, the lower the value of the $ED_{50}$, the greater is the chemotactic activity.

TABLE 1

| Peptide | Chemotactic Activity $ED_{50} \pm SE$ |
|---|---|
| F—Met—Leu—Phe—OH | $7.0 \pm 1.7 \times 10^{-11}$ |
| f—Met—Met—Phe—OH | $2.1 \pm 0.49 \times 10^{-10}$ |
| f—Met—Met—Met—Met—OH | $3.0 \pm 0.13 \times 10^{-10}$ |
| f—Nle—Leu—Phe—OH | $6.6 \pm 1.2 \times 10^{-10}$ |
| f—Met—Leu—Phe—Lys—OH | $7.0 \pm 1.0 \times 10^{-10}$ |
| f—Met—Leu—OH | $4.0 \pm 0.45 \times 10^{-7}$ |
| f—Met—Phe—OH | $4.1 \pm 0.95 \times 10^{-7}$ |

EXAMPLE 3

Assay of Lysosomal Enzyme Secretion-Inducing Activity

Washed neutrophils as described in Example 2 above, were resuspended to a final concentration of $1 \times 10^7$/ml in Hanks' buffer containing 2 mg/ml of bovine serum albumin and 10 $\mu$g/ml cytochalasin B (Aldrich Chemical Co., Milwaukee, Wis.). The cytochalasin B was diluted from a stock solution containing 4 mg/ml in dimethyl sulphoxide. The dimethyl sulphoxide remaining after dilution was shown not to affect the release. In duplicate, 0.5 ml of cell suspension was added to 0.5 ml of fourfold serial dilutions of peptide in $12 \times 75$ mm test tubes at 4° C. The mixtures were then incubated for five minutes at 37° C. (the release is completed in one minute of less under these conditions) and the tubes centrifuged at 2500 rpm (1400 g) for five minutes at 4° C. The supernatants were removed and aliquots taken for measurement of lactic dehydrogenase, lysozyme, and $\beta$-glucuronidase as described by Becker et al (Mechanisms in Allergy, Marcel Dekker Inc., New York, 1973, Page 339).

The total concentration of enzyme was measured by lysing the cells with buffer containing 0.1 percent Triton X-100 (Beckmann Instruments, Inc., Fullerton, Calif.). The units of enzyme activity were calculated as described by Becker et al (J. Immunol., Volume 112, Page 2055, 1974). The lactic dehydrogenase of each supernate was measured to insure that the peptides induced no release of this cytoplasmic marker. No release was found in any instance.

The ability of each peptide to induce lysosomal enzyme release was assayed essentially as described for chemotactic activity in Example 2 above. The lysozyme or $\beta$-glucuronidase activity released into the supernate at each concentration a given peptide plotted against the logarithm of the molar concentration of the peptide gave rise to a sigmoidal dose-response curve. As with chemotactic activity, in a given experiment, the curves were parallel in their linear portions and showed the same maximum. The lysosomal enzyme-inducing activity for each peptide was obtained from the dose-response curve as its $ED_{50}$, i.e., the molar concentration of peptide causing 50 percent of the maximal release of either lysozyme or $\beta$-glucuronidase. The results of this assay are reported in Table 2 below, in the same manner for the same N-formyl peptides as listed in Table 1. Again, the lower the value of the $ED_{50}$, the greater is the lysosomal enzyme secretion-inducing activity.

TABLE 2

Lysosomal Enzyme Secretion-Inducing Activity

| Peptide | $ED_{50} \pm SE$ Lysosyme | B-Glucoronidase |
|---|---|---|
| f—Met—Leu—Phe—OH | $2.4 \pm 0.31 \times 10^{-10}$ | $2.6 \pm 0.32 \times 10^{-10}$ |
| f—Met—Met—Phe—OH | $1.9 \pm 0.4 \times 10^{-9}$ | $1.8 \pm 0.24 \times 10^{-9}$ |
| f—Met—Met—Met—Met—OH | $2.4 \pm 0.34 \times 10^{-9}$ | $3.0 \pm 0.73 \times 10^{-9}$ |
| f—Nle—Leu—Phe—OH | $1.5 \pm 0.2 \times 10^{-9}$ | $1.9 \pm 0.2 \times 10^{-9}$ |
| f—Met—Leu—Phe—Lys—OH | $1.7 \pm 0.5 \times 10^{-9}$ | $1.9 \pm 0.3 \times 10^{-9}$ |
| f—Met—Leu—OH | $1.7 \pm 0.17 \times 10^{-6}$ | $1.9 \pm 0.21 \times 10^{-6}$ |
| f—Met—Phe—OH | $1.5 \pm 0.39 \times 10^{-6}$ | $2.0 \pm 0.42 \times 10^{-6}$ |

EXAMPLE 4

Test for True Chemotaxis

Increased penetration of cells into or through the filter of a Boyden chamber system under the stimulus of a chemical agent is generally taken as indicating the chemotactic activity of the agent. Zigmond and Hirsch (J. Exp. Med., Volume 137, Page 387, 1973) have pointed out that the increased migration could result from a response directed by the chemical gradient, that is from chemotaxis, or from increased random locomotion or both. These authors have described a technique for determining if the movement of the cells into the filter of a Boyden chamber system under the influence of different gradients is greater than could be expected on the basis of increased rates of locomotion alone and to that extent is due to a true chemotactic response. The Zigmond and Hirsch technique was carried out for f-Met-Leu-Phe-OH, as representative of the N-formyl peptides of the present invention, in order to determine whether or not the peptides are truly chemotactic.

In testing f-Met-Leu-Phe-OH for true chemotaxis, $5 \times 10^6$/ml of washed peritoneal neutrophils obtained twelve hours after the administration of 0.1 percent glycogen were suspended in varying concentrations of the peptide and placed in the upper compartment of a modified Boyden chamber. The cells were separated from the bottom compartment containing varying concentrations of the same peptide by a 3.0 $\mu$m pore size filter. Duplicate chambers were incubated sixty minutes at 37° C. The filters were fixed and processed as usual. Using the micrometer of the fine adjustment of the microscope, the distance was measured from the top of the filter to the farthest plane of focus still containing two cells. This distance was determined across five fields and averaged. For reversibility studies, cells were incubated thirty minutes at 37° C. in varying concentrations of the peptide before washing with buffer or saline and testing in fresh medium. The test results were analyzed as described by Zigmond and Hirsch. Over the concentration ranges employed, the effect of the peptide on locomotion was rapid and largely reversible. The peptide stimulated random movement of the neutrophil as shown by the penetration obtained when no gridient was present.

Comparison of experimental values with predicated values established that the peptide was truly chemotactic, since the cells moved significantly farther than predicted (greater than 10 $\mu$m) when the concentration of peptide below was greater than above the filter (positive gradient) and not as far as predicted when the reverse was the case (negative gradient).

EXAMPLE 5

Synthesis and Characterization of Chemotactic-Antibiotic Conjugates

The following are the abbreviations used:
FMLP, formyl-methionyl-leucyl-phenylalanine
SDZ, sulfadiazine
BOC, t-butoxycarbonyl
TFA.H, trifluoracetic acid salt
AgSDZ, silver sulfadiazine
DMSO, dimethylsufoxide
DMF, dimethylformamide
PMN, polymorphonuclear leukocyte
MN, monocyte
$ED_{50}$, molar concentration yielding 50% maximal chemotactic activity
$ID_{50}$, molar concentration which displaces 50% of a labeled attractant from the cell receptor
MIC, minimal inhibitory concentration

Synthesis of FMLP-AgSDZ

The compound, FMLP-AgSDZ, was obtained by a series of coupling reactions using the mixing anhydride procedure in solution (Vaughan, J. R. Jr., J. Am. Chem. Sol. 74 6137 (1952). The procedure is outlined in FIG. 1.

In the first step, Boc-Phe-SDZ was prepared as follows: Boc-Phe-OH (10 mMol) and triethylamine (10 mMol) in DMF (25 ml) were cooled to $-20°$. Trimethylacetyl chloride (10 mMol) was added with stirring under anhydrous conditions. After 10 min. at this temperature, SDZ (10 mMol) in DMF (20 ml) and pyridine (10 ml) were added to the mixture, which was then allowed to come to room temperature. After one day, the product was precipitated by the addition of saturated $NaHCO_3$ solution and collected by filtration. The material was washed with water, dried, and recrystallized from ethyl acetate.

In the second step, Boc-Phe-SDZ was deprotected by the addition of 2 M HCl in ethyl acetate to give the hydrochloride salt, HCl.H-Phe-SDZ. This compound was then converted to Boc-Leu-Phe-SDZ by the addition of Boc-Leu in the mixed anhydride reaction (Step 1). In a similar manner were added successively Met-OH and HCOOH. The product, FMLP-SDZ, was recrystallized from acetonitrile. The purified material was converted to FMLP-AgSDZ by adding aqueous $AgNO_3$ to a solution of the conjugate in DMSO at pH 7.5.

Synthesis of fMet-Leu-Sulfadiazine 1 mM of fMet-Leu-OH was dissolved in 5 ml of dry dimethylformamide (DMF). The mixture was kept anhydrous, and 1 mM triethylamine (free base) was added. The material was then immersed in a salt ice-bath at a temperature from −20° to −20°. After 5 minutes exactly 1 mM of Isobutyl chlorocarbonate was added. A precipitate formed rapidly and the mixture was kept in the cold bath for 10 minutes with intermittent shaking. Some yellow color developed. In 2 ml of DMF, 1 mM of sulfadiazine (SDZ) was added to the cold mixture was shaking. The yellow color deepened and the stoppered mixture was allowed to come to room temperature. The pH gradually fell to 3.8 and the mixture was warmed at 50° for 5 minutes. The mixture was then diluted with 100 ml cold water, and the resulting precipitate centrifuged, washed once with cold water, and dried in vacuo.

TLC of the mixture (silica gel; diethylamine-methanol-cyclohexane:10-30-60) showed the product to be virtually free of SDZ. The crude product was washed ×2 with small amounts of cold 0.05 M Na HCO3, then ×2 with cold water and dried in vacuo. The material was then recrystallized in acetone-pet. ether (B.P. 30°-60°). This material gave 1 UV absorbent zone on TLC, was separable from starting materials on TLC, and produced a chemotactic response in neutrophils as potent as fMet-Leu-OH. It also was as effective as fMet-Leu-OH in the receptor binding assay. The yield was approximately 30%.

The FMLP-SDZ was characterized by thin layer chromatography. It was homogeneous in three solvent systems as shown in Table 3.

TABLE 3

| | | $R_f$ |
|---|---|---|
| (1) CHCl$_3$/CH$_3$OH/AcOH | (90:5:5) | 0.50 |
| (2) CHCl$_3$/CH$_3$OH/AcOH | (85:10:5) | 0.95 |
| (3) EtAC/PYr/AcOH/H$_2$O | (90:20:6:11) | 0.77 |

Upon hydrolysis in 6 N hydrochloric acid and phenol at 111° C. for 18 hr. the amino acid composition of the f-ML-P-AgSDZ yielded only met, leu and phe in equimolar ratios. The decomposition point for FMLP-AgSDZ was 228° C. The FMLP-SDZ was soluble in DMSO, DMF and 1 molar NaOH. The F-MLP-AgSDZ was only slightly soluble in DMSO.

The antimicrobial activity of the f-met-leu-phe-silver sulfadiazine was tested on two bacterial indicator strains as shown in Table 4. The minimal inhibitory concentration of silver sulfadiazine alone was slightly lower then that of the FMLP-AgSDZ. However this is due in part to the higher molecular weight of the peptide-sulfidiazine complex.

TABLE 4

| Antimicrobial Activity of FMLP—AgSDZ:MIC at 24h in μg/m | | | |
|---|---|---|---|
| Pseudomonas aeruginosa, strain VA 134 | | Pseudomonas aeruginsa, strain Mangalore | |
| EXPT | AgSDZ | FMLP—AgSDZ | AgSDZ | FMLP—AgSDZ |
| 1 | 40 | 20 | 20 | 40 |
| 2 | 40 | 80 | 40 | 40 |
| 3 | 40 | 80 | 40 | 80 |

The chemotaxis of F-met-leu-phe-silver sulfadiazine complex and FMLP was measured on human monocytes and on rabbit polymorphonuclear leukocytes. The molar concentration of peptide complex yielding 50% maximal activity was measured three times as shown in Table 5. The chemotactic peptide alone was more active then the peptide-sulfadiazine complex, however, the FMLP-AgSDZ was still highly active as a chemotactic agent.

TABLE 5

| CHEMOTAXIS OF FMLP—AgSDZ FOR HUMAN MN AND RABBIT PMN (ED$_{50}$, M conc giving 50% maximal activity) | | |
|---|---|---|
| EXPT | FMLP | FMLP—AgSDZ |
| HUMAN MN | | |
| 1 | $8.8 \times 10^{-9}$ | $1.5 \times 10^{-8}$ |
| 2 | $3.2 \times 10^{-9}$ | $3.1 \times 10^{-8}$ |
| 3 | ND | $7.2 \times 10^{-9}$ |
| RABBIT PMN | | |
| 1 | $1.5 \times 10^{-10}$ | $2.5 \times 10^{-10}$ |
| 2 | $3.0 \times 10^{-10}$ | $7.0 \times 10^{-10}$ |

Figure 2:
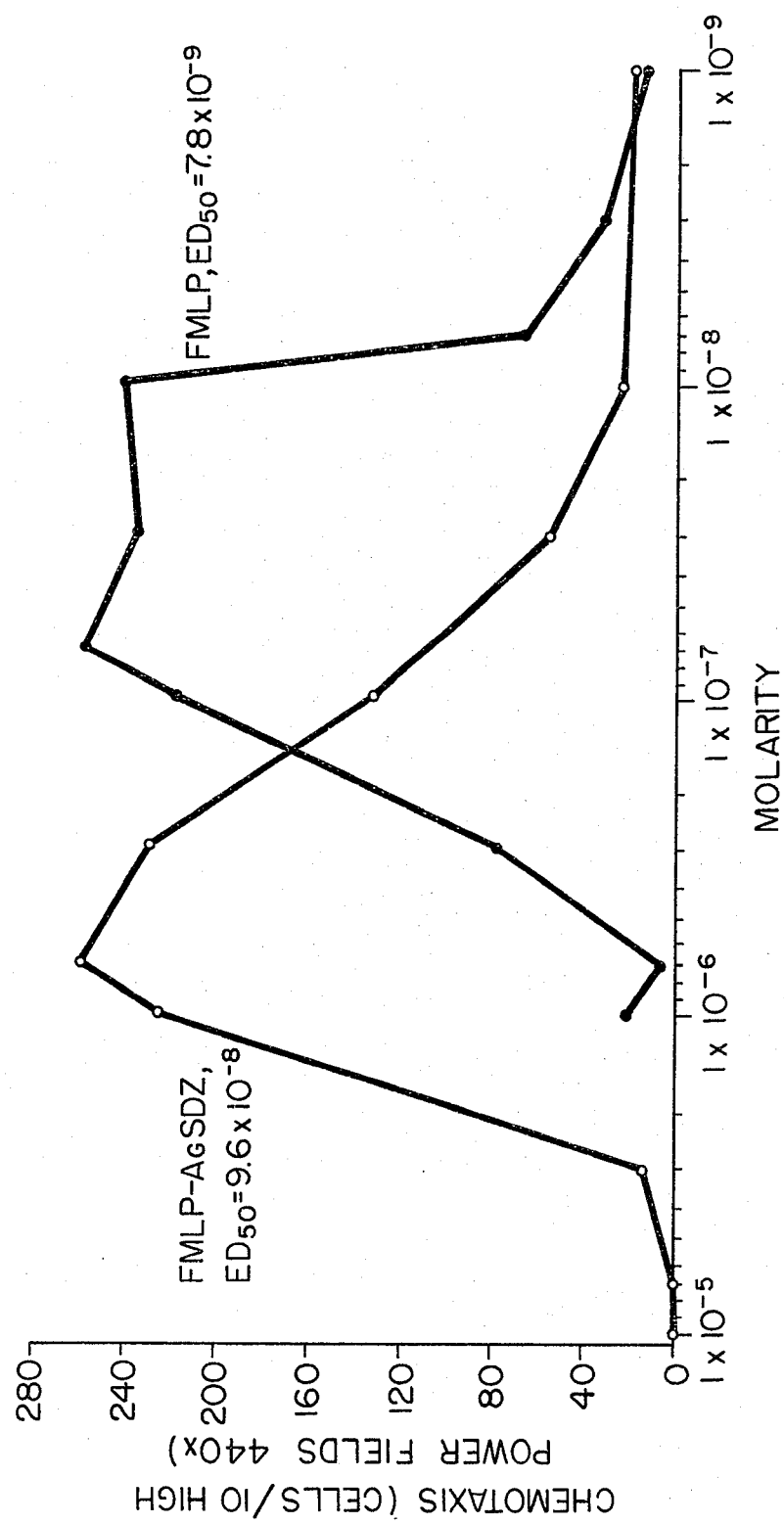
FIG. 2-Chemotactic activity of FMLP-AgSDZ and FMLP for human polymorphonuclear leukocytes.

The chemotaxis of both FMLP-AgSDZ and FMLP for human polymorphonuclear leukocytic was measured at various concentrations of FMLP-AgSDZ. This is illustrated in FIG. 2. The ED$_{50}$ for FMLP-AgSDZ was $9.6 \times 10^{-8}$ and the ED$_{50}$ for FMLP was $7.8 \times 10^{-9}$.

Figure 3:
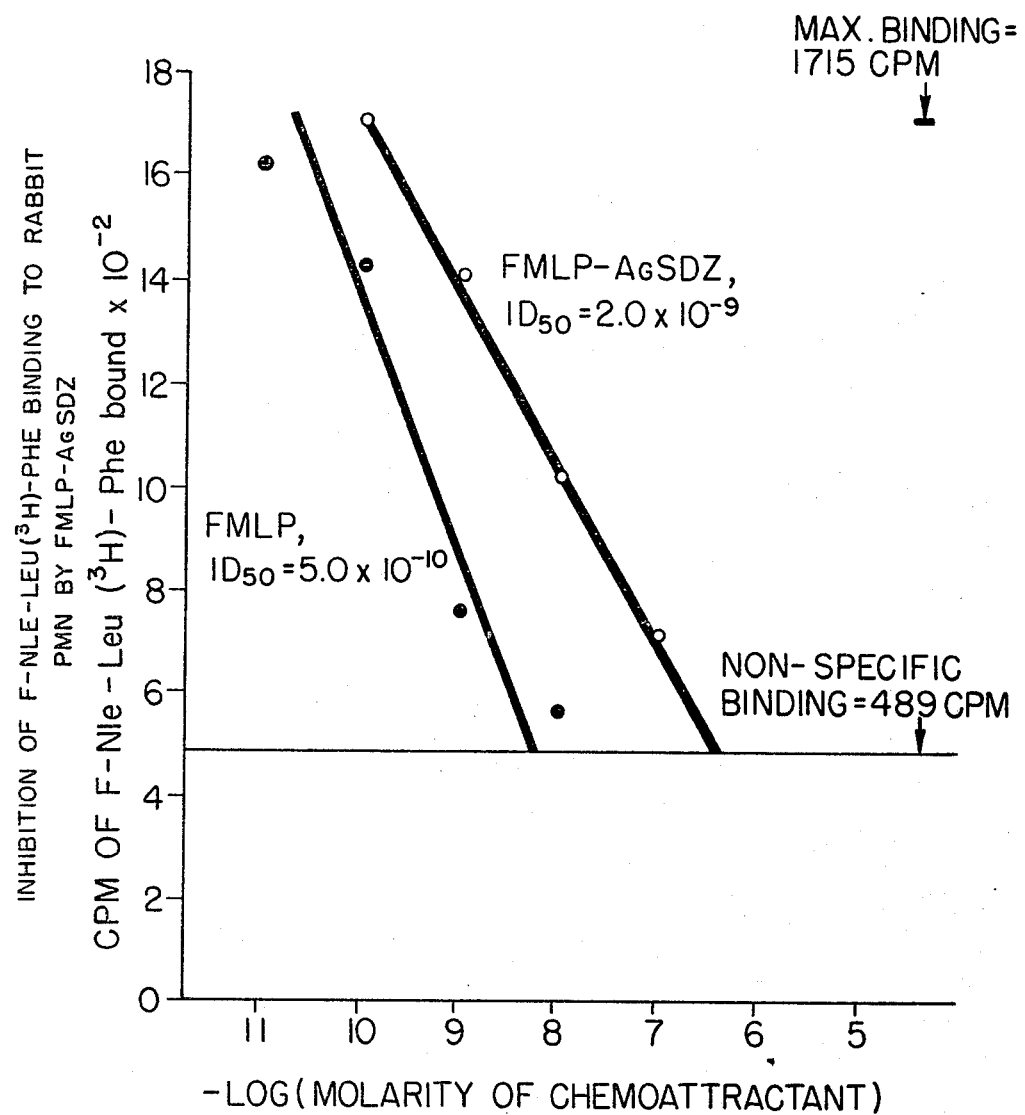
FIG. 3-Inhibition of F-Nle-leu ($^3$H)PHE binding to rabbit PMN by FMLP-AgSDZ.
Figure 4:
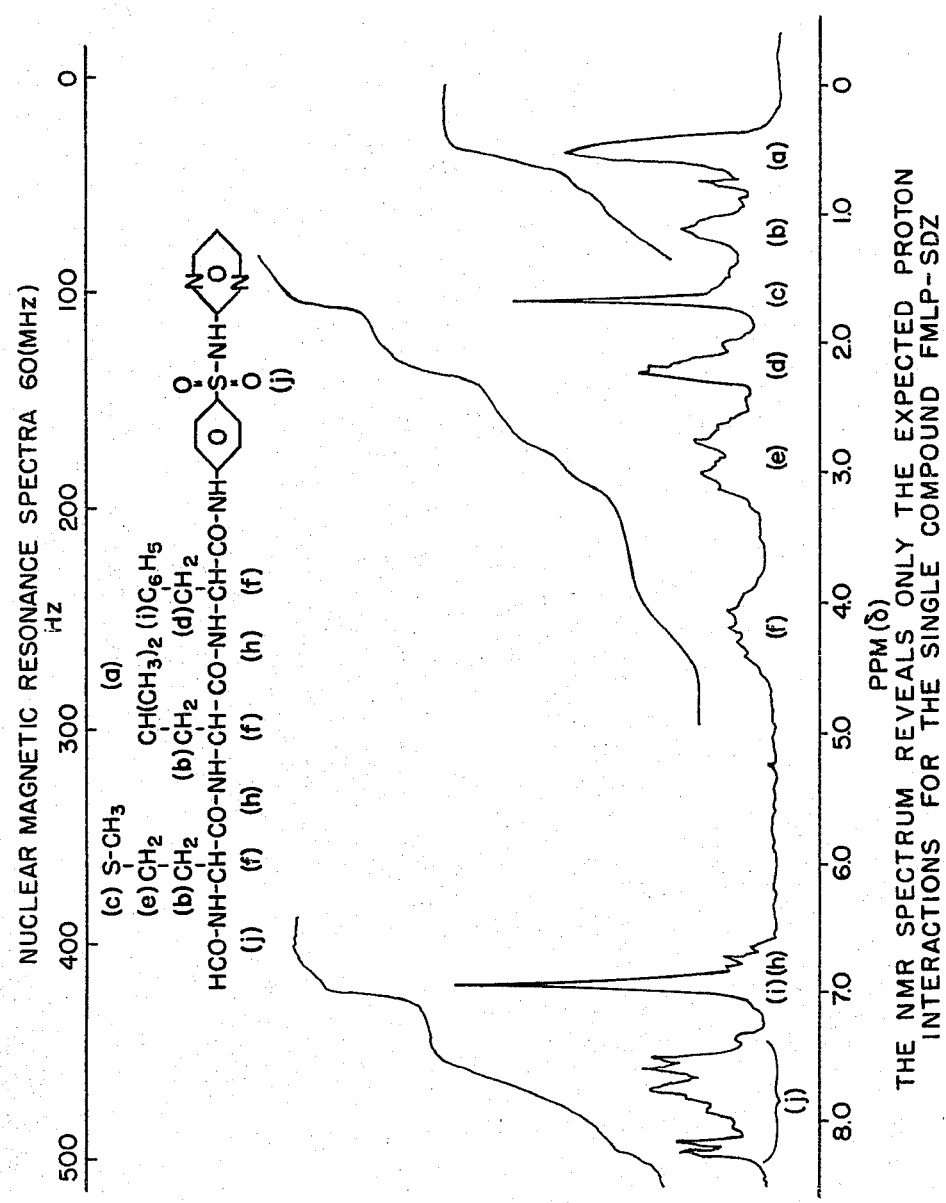
FIG. 4-The NMR spectrum of FMLP-AgSDZ.

The binding of both FMLP and FMLP-AgSDZ to the surface receptor of rabbit polymorphonuclear leukocytes is shown in FIG. 3. The molar concentration which displaced 50% of a labeled attractant from the cell receptor was shown to be $5 \times 10^{-10}$ molar for FMLP and $2 \times 10^{-9}$ for FMLP-AgSDZ. The nuclear magnetic resonance for the FMLP-AgSDZ is shown in FIG. 4 confirming the structure as expected.

The FMLP-Ag-SDZ is active both as a leukoattractant and as an antimicrobial agent. It was prepared by a mixed anhydride reaction to form FMLP-SDZ. It was then converted to FMLP-AgSDZ by reaction with silver nitrate. The purity was demonstrated by amino acid analysis, thin layer chromatography and nuclear magnetic resonance.

The chemotactic properties of both FMLP and FMLP-AgSDZ was measured on both rabbit and human polymorphonuclear leukocytes and on human monocytes. This activity is summarized below:

TABLE 6

| CHEMOTACTIC ACTIVITY (M concentration giving 50% max activity, ED$_{50}$) | | | |
|---|---|---|---|
| Agent | Rabbit PMN | Human PMN | Human MN |
| FMLP | $1 \times 10^{-10}$ | $1.1 \times 10^{-8}$ | $8.8 \times 10^{-9}$ |
| FMLP—AgSDZ | $2.5 \times 10^{-10}$ | $7.8 \times 10^{-8}$ | $1.5 \times 10^{-8}$ |

FMLP-AgSDZ was a potent leukoattractant, although slightly less active than FMLP for all three cell types.

FMLP-AgSDZ and FMLP displaced 50% of a radiolabeled f-peptide ligand (ID$_{50}$) from PMN's at simlar concentrations as shown in FIG. 2. This indicated that both compounds stimulate chemotaxis via the same receptor.

Antimicrobial activity was assayed by the MIC Technique using 4 strains of Pseudomonas aeruginosa. All strains were inhibited at 40 μm/ml AgSDZ and 80 μm/ml FMLP-AgSDZ, thereby indicating that the conjugate retains potent antimicrobial activity.

Based upon the preceding analysis it has been shown that the compound FMLP-AgSDZ is a superior agent for treating localized infections because it simultaneously promotes leukocyte accumulation and inhibits bacterial growth.

EXAMPLE 6

Elemental Analysis of Conjugate

The following is the result of an elemental analysis of the f-met-leu-phe-sulfadiazine silver conjugate, the observed elemental composition corresponds to that expected for the conjugate within experimental error.

TABLE 7

|          | % C   | % H  | % N   | % S  | % Ag  |
|----------|-------|------|-------|------|-------|
| Expected | 48.13 | 4.95 | 12.67 | 7.90 | 13.94 |
| Observed | 44.96 | 4.94 | 12.05 | 8.01 | 15.47 |

The carbon, hydrogen, nitrogen were analyzed with an elemental analyzer, silver by atomic absorption and sulfur by combustion and synthesis of sulfur dioxide.

The methods used are standard procedures used in analytical chemistry. These procedures can be found in the following procedures hereby incorporated by reference.

"Analytical Methods for the 240 CHN Analyzer" by Perkin Elmer Co. Norwalk, Conn.

"An Automatic Organic Elemental Microanalyzer", Condon, R. D., Microchemical J. 10, 408 (1966).

Microchemical Journal 15, 590-597 (1970) A Direct Comparison of Pregl, Dumas, P-E, FM CHN procedures.

Ingram, G, Combustion of Organic Compounds by their ignition in oxygen for the microdetermination of some elements. In "Proceedings, 1961-International Symposium on Microchemical Techniques. Microchemical Journal Synmposium Series, Vol. II, Microchemical Techniques" (N. D. Cheronis, ed.) pp. 495-526, Wiley (Interscience), NY 1962.

The determination of metals by atomic absorption spectrophotometry was performed in the following manner. Samples of organic materials are decomposed using an acid digestion or by ashing depending on the nature of the material. The concentration of the element(s) of interest is determined by atomic absorption using the procedure in *Analytical Methods for Atomic Absorption Spectrophotometry*, Perkin-Elmer, Norwalk, Conn., herein incorporated by reference.

Sulfur is determined by high temperature (2500° F.) combustion in oxygen and the $SO_2$ produced is measured by IR. A Leco SC-32 instrument is used for the determination. The following describes the method for such determination.

"A Rapid Method for the Determination of Sulfur in the presence of Chlorine" by: Bernard E. Nael Research Laboratories General Motors Corporation.

"Instructions for Analysis in Hydrocarbons by Leco High Frequency Combustion Titration Procedure" LECO publication; St. Joseph, Mich. The preceding 2 publication are herein incorporated by reference.

EXAMPLE 7

Admixtures of F-Met-Leu-Pheo and silver sulfadiazine

Admixtures of chemotactic peptides and silver sulfadiazine are not functionally active as leukoattractants. When not physically coupled it is not possible to obtain bifunctional activity simply by mixing a f-met peptide with sulfadiazine or its silver salt.

Sulfadiazine inhibits the chemotactic properties of both FMLP and FML as shown in Table 8 and Table 9. The mixture of sulfadiazine inhibited the chemotactic migration of the polymorphonecular leukocytes and monocytes.

TABLE 8

EFFECT OF SULFADIAZINE ON THE CHEMOTACTIC ACTIVITY OF FML

|              |                  | % Inhibition |      |
|--------------|------------------|--------------|------|
| [F—Met—Leu]  | Sulfadiazine (μg)| PMN          | MN   |
| $10^{-3}$    | 0                | —            | —    |
|              | 5                | 19.0         | 2.5  |
|              | 25               | 38.0         | 13.0 |
|              | 50               | 48.7         | 36.7 |
|              | 100              | 73.3         | 43.3 |
|              | 250              | 83.9         | 98.0 |
| $10^{-4}$    | 0                | —            | —    |
|              | 5                | 1.0          | 20.0 |
|              | 25               | 14.0         | 17.5 |
|              | 50               | 37.5         | 17.0 |
|              | 100              | 53.0         | 60.0 |
|              | 250              | 41.0         | 97.5 |

TABLE 9

EFFECT OF SULFADIAZINE ON THE CHEMOTACTIC ACTIVITY OF FMLP

|                   |                   | % Inhibition |      |
|-------------------|-------------------|--------------|------|
| [F—Met—Leu-]-Phe  | Sulfadiazine (μg) | PMN          | MN   |
| $10^{-6}$         | 0                 | —            | —    |
|                   | 5                 | 10.0         | 22.5 |
|                   | 25                | 8.0          | —    |
|                   | 50                | 39.5         | 21.0 |
|                   | 100               | 49.0         | 82.0 |
|                   | 250               | —            | —    |
| $10^{-7}$         | 0                 | —            | —    |
|                   | 5                 | 16.8         | 14.6 |
|                   | 25                | 18.0         | —    |
|                   | 50                | 65.8         | 13.7 |
|                   | 100               | 70.8         | 41.7 |
|                   | 250               | 88.0         | 96.6 |

The chemotaxis experiments were performed in the following manner.

The experiments in Table 8 and 9 were performed in modified Boyden chemotaxis chambers. The neutrophil (PMN) experiments used 3μ nitrocellulose filters and the monocyte (MN) experiments used 5μ polycarbonate filters. PMNs and MNs were prepared from human peripheral blood by Ficoll-Hypaque and dextran sedimentation techniques. The chemoattractants f-met-leu (fML) and f-met-leu-phe (fMLP) were mixed with sulfadiazine in the final concentrations indicated in the tables using Gey's balanced salt solution and gelatin veronal buffer as diluents. PMN experiments were incubated at 37° C. for 3 hours, MN experiments for 90 minutes. After this the filters were removed and stained and counted visually with a microscope. References for these techniques are:

Altman L. C., Boetcher D. A., Goodwin R. H.: Leukocyte Chemotaxis, manual published by the Nuclepore Corporation, 1976.

Synderman R. Altman L. C., Hausman M. C., Mergenhagen S. E.: Human mononuclear leukoctye chemotaxis: quantitative assay for humoral and cellular chemotactic factors. J. Immuno. 108:857, 1972.

TABLE 10

EFFECT OF FML ON THE ANTIMICROBIAL ACTIVITY OF SILVER SULFADIAZINE (Ag—SDZ)

| Test strain: *E. coli* Disc Content | Zone Diameter (mm) |
|---|---|
| Ag—SDZ 25 μg/FML $10^{-4}$ M | 33.5 |
| Ag—SDZ 10 μg/FML $10^{-4}$ M | 28.8 |
| Ag—SDZ 5 μg/FML $10^{-4}$ M  | 22.8 |

TABLE 10-continued

EFFECT OF FML ON THE ANTIMICROBIAL ACTIVITY OF SILVER SULFADIAZINE (Ag—SDZ)

| Test strain: E. coli Disc Content | Zone Diameter (mm) |
|---|---|
| Ag—SDZ 25 µg/FML $10^{-5}$ M | 31.8 |
| Ag—SDZ 10 µg/FML $10^{-5}$ M | 27.2 |
| Ag—SDZ 5 µg/FML $10^{-5}$ M | 24.6 |
| FML | 6.0 |
| Pyridine | 6.0 |

TABLE 11

EFFECT OF FML ON THE ANTIMICROBIAL ACTIVITY OF SILVER SULFADIAZINE (Ag—SDZ)

| Test Strain: P. aeruginosa Disc Content | Zone Diameter (mm) |
|---|---|
| Ag—SDZ 25 µg | 28.5 |
| Ag—SDZ 25 µg/FML $10^{-4}$ N | 27.7 |
| FML | 6.0 |
| Pyridine | 6.0 |

When F-met-leu or F-mat-leu-phe are physically mixed with the silver sulfadiazine there was no interference with the action of the silver sulfadiazine as shown in Tables 10–14. Neither silver sulfadiazine or sulfadiazine is effected by the presence of the chemopeptides. In these tables antimicrobial activity is expressed as inhibitory zone size as performed by the Kirby-Bauer assay. The 6 mm zone shown by pyridine, f-met-leu and f-met-leu-phe indicates no inhibition since this is the diameter of the disc used in the assay.

TABLE 12

EFFECT OF FMLP ON THE ANTIMICROBIAL ACTIVITY OF SULFADIAZINE (SDZ)

| Test strain: E. coli Disc Content | Zone Diameter (mm) |
|---|---|
| SDZ 25 µg | 32.0 |
| SDZ 25 µg/FMLP $10^{-6}$ M | 31.9 |
| SDZ 10 µg | 28.0 |
| SDZ 10 µg/FMLP $10^{-6}$ M | 27.4 |
| FMLP $10^{-6}$ M | 6.0 |
| Pyridine | 6.0 |

TABLE 13

EFFECT OF FMLP ON THE ANTIMICROBIAL ACTIVITY OF SILVER SULFADIAZINE (Ag—SDZ)

| Test strain: E. coli Disc Content | Zone Diameter (mm) |
|---|---|
| Ag—SDZ 25 µg | 32.2 |
| Ag—SDZ 25 µg/FMLP $10^{-6}$ M | 32.4 |
| Ag—SDZ 10 µg | 23.8 |
| Ag—SDZ 10 µg/FMLP $10^{-6}$ M | 23.9 |
| FMLP $10^{-6}$ M | 6.0 |
| Pyridine | 6.0 |

TABLE 14

EFFECT OF FMLP ON THE ANTIMICROBIAL ACTIVITY OF SILVER SULFADIAZINE (Ag—SDZ)

| Test strain: P. aeruginosa Disc Content | Zone Diameter (mm) |
|---|---|
| Ag—SDZ 25 µg | 18.6 |
| Ag—SDZ 25 µg/FMLP $10^{-6}$ M | 18.6 |
| Ag—SDZ 10 µg | 16.2 |
| Ag—SDZ 10 µg/FMLP $10^{-6}$ M | 16.8 |
| FMLP $10^{-6}$ M | 6.0 |
| Pyridine | 6.0 |

The Kirby-Bauer assay described below can be found in the following publications herein incorporated by reference:

Bauer A. W., Kirby W. M. M., Sherris J. C., Turck M.: Antibiotic susceptibility testing by testing by a standardized single disk method. Am. J. Clin. Pathol. 45:493–496, 1966.

Barry A. L., Thornsberry C.: Susceptibility testing: Diffusion testing procedures in Manual of Clinical Microbiology, Third Edition, Chapter 44, American Society of Microbiology, Washington, D.C., 1980, p 463–474.

The experiments in Tables 10–14 were performed using the following bacteria, media and experimental protocol:

The bacteria were *Escherichia coli* ATCC 25922 and *Pseudomonas aeruginosa* ATCC 27835. These strains are used for quality control in antibiotic susceptibility testing.

The media was Trypticase soy agar (Baltimore Biological Laboratories, BBL) used as a general growth medium. Broth media was Brain heart infusion broth (BBL) for *E. coli* and medium 81 [trypticase soy broth without dextrose plus 1% potassium nitrate] for *P. aeruginosa*.

Antimicrobial susceptibility was tested on M9 medium [a glucose minimal salts medium (Miller, 1972)] solidified with 1.5% agar (Difco) for the base or 0.7% agar for overlay.

The following is the experimental protocol: Broth cultures of *E. coli* or *P. aeruginosa* were grown overnight in broth at 35° C. Cultures were diluted to visually match a 0.5 McFarland turbidity standard (Matsen and Barry, 1974); the numbers of organisms in this suspension ordinarily were $\simeq 10^8$ viable cells per ml. Ten microliter (ul) was inoculated into 10 ml. of 0.7% M9 agar that was melted and cooled to 46°–50° C. This was overlaid onto a 50 ml base of 1.5% M9 agar in 15 cm diameter petri dishes. The agar overlay was allowed to harden at room temperature for 30 min. Antimicrobial tests disks were placed on the surface of the agar, and the plates were incubated overnight at 35° C. Diameters of zones of inhibition of bacterial growth were measued with a vernier caliper and recorded to the nearest 0.1 mm.

The antimicrobic paper test disks were prepared by spotting 25 ul of antimicrobic or antimicrobic/peptide solutions to give the concentrations shown in the appropriate tables. Sterile disks were purchased from BBL.

It was not possible to obtain bifunctional activity by simply mixing an f-met-peptide with sulfadiazine or its silver salt. To achieve this end of new chemical compound was required. This new compound was f-met-leu-phe-silver sulfadiazine.

EXAMPLE 8

Rat and Mouse Burn Model Systems

The FMLP-AgSDZ can be used to treat burns on experimental animals as follows:

The mouse model uses 18–22 gram female Swiss-Webster mice. The animals receive a 10-second ethanol flame burn using an asbestos template. Depending on the size of the hole cut in the template the total body surface burn can vary from 15–30%. The burn is then infected by subcutaneously injecting 0.5 ml of suspension of *Pseudomonas aeruginosa* strain M2 organisms at various concentrations into the wound area. An alternative mouse burn model which we have not used employs the same strain and weight animals but the burn is inflected by immersing the animals in 70° C. water for 7 seconds. The lower one-third of the body and tail are burned.

Inoculation of bacteria is done 1 hour postburn by dipping the tails into an 18-hour nutrient broth culture of *Pseudomonas aeruginosa* organisms at an optical density of 0.35 to 660 nanometers. This equals approximately $5 \times 10^7$ organisms/ml.

This procedure is extensively described in the following publications:

Stiertiz D. D., Holder I. A.: Experimental studies of the pathogenesis of infections due to *Pseudomonas aeruginosa*: Description of a burned mouse model. J. Infect. is. 131(6):688–691, 1975.

Fox C. J., Jr, Sampath A. C., Stanford J. W.: Virulence of Pseudomonas infection in burned rats and mice. Arch Surg 101:508–512, 1970.

The rat burn model uses 190–210 gram female Sprague-Dawley rats. The animals are strapped into a template after shaving their back hair and dipped for 10 seconds into boiling water. With the standard template a 15–18% total body surface burn is produced. The usual method for infecting the burn is to topically apply 1 ml of *Pseudomonas aeruginosa* organisms at an optical density of 0.17 at 540 nanometers. This equals $1 \times 10^8$ organisms. We have used many stains of Pseudomonas, but the most common has been VA134.

This procedure is describe in Walker H. L., Mason A. D.: A standard animal burn. J. Trauma 8(6):1049–1051, 1968.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An N-formyl peptide-antibiotic complex selected from the group consisting of f-Met-Leu-Phe-R, f-Met-Met-Phe-R, f-Met-Met-Met-R, f-Nle-Leu-Phe-R, f-Met-Leu-Phe-Lys-R, and their pharmaceutically acceptable non-toxic acid addition salts, wherein R is an agent selected from the group consisting of sulfonamide antimicrobial agents, silver containing antimicrobial agents, and antifungal agents.

2. The N-formyl peptide-antibiotic complex of claim 1, wherein R is silver sulfadiazine, which is f-Met-Leu-Phe-silver sulfadiazine.

3. The N-formyl peptide-antibiotic complex of claim 1, wherein R is silver sulfadiazine, which is f-Met-Met-Phe-silver sulfadiazine.

4. The N-formyl peptide-antibiotic complex of claim 1, wherein R is silver sulfadiazine, which is f-Met-Met-Met-Met-silver sulfadiazine.

5. The N-formyl peptide-antibiotic complex of claim 1, wherein R is silver sulfadiazine, which is f-Nle-Leu-Phe-silver sulfadiazine.

6. The N-formyl peptide-antibiotic complex of claim 1, wherein R is silver sulfadiazine, which is f-Met-Leu-Phe-Lys-silver sulfadiazine.

7. The N-formyl peptides of claim 1 wherein said antifungal agent is miconazole.

8. The N-formyl peptides of claim 1 wherein said antifungal agent is clotrimazole.

9. The N-formyl peptides of claim 1 wherein said antifungal agent is nystatin.

10. The N-formyl peptides of claim 1 wherein said antifungal agent is amphotericin B.

11. A method of treating septic trauma comprising the application of a pharmacologically effective amount of the compounds of claim 1.

12. A method of treating burns comprising the application of a pharmacologically effective amount of formyl-methionyl-leucyl-phenylalanine-silver sulfadiazine.

13. A method of treating a burn victim comprising the application of a pharmacologically effective amount of the compounds of claim 1.

14. A method of treating fungal infections comprising the application of a pharmacologically effective amount of the compounds of claim 1.

15. A method of treating as in claim 12 wherein the pharmacologically effective amount of chemotactic-antibiotic complex is supplied topically to create a concentration gradient wherein the concentration is higher at the trauma site and progressively lower in the surrounding tissue.

* * * * *

UNITED STATES PATENT AND TRADEMARK OFFICE
CERTIFICATE OF CORRECTION

PATENT NO. : 4,427,660
DATED : March 7, 1985
INVENTOR(S) : Elliott Schiffman, et al.

It is certified that error appears in the above—identified patent and that said Letters Patent are hereby corrected as shown below:

Column 11, line 3, "-20 to -20°." should read as -- -20 + -10° --.
Column 15, line 23, "F-mat-leu-phe" should read as -- F-met-leu-phe --.
Claim 1, column 17, line 43, "f-MET-MET-MET-R" should read as-- f-Met-Met-Met-Met-R --.

Signed and Sealed this

Twenty-fifth Day of June 1985

[SEAL]

Attest:

DONALD J. QUIGG

Attesting Officer     Acting Commissioner of Patents and Trademarks